US00PP10931P

United States Patent [19]

Zary

[11] Patent Number: Plant 10,931

[45] Date of Patent: Jun. 1, 1999

[54] FLORIBUNDA ROSE PLANT NAMED 'JACESS'

[76] Inventor: Keith W. Zary, 326 Clearview St., Thousand Oaks, Calif. 91360

[21] Appl. No.: 08/800,050

[22] Filed: Feb. 14, 1997

[51] Int. Cl.[6] ..... A01H 5/00

[52] U.S. Cl. ..... Plt./23

[58] Field of Search ..... Plt./23

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class, having consistent production of roses in clusters of 5 to 7 flowers; long vase life; high petal count; and high production per square meter of greenhouse.

1 Drawing Sheet

The present invention relates to a new and distinct variety of rose plant of the floribunda class which was originated by me by crossing the variety INTERprince, U.S. Plant Pat. No. 8,102, with an unnamed floribunda seedling.

The primary objective of this breeding was to produce a new rose variety having the good clustering ability and production of the female parent combined with the higher petal count and larger flowers of the male unnamed light pink floribunda seedling. The objective was substantially achieved, along with other desirable improvements, as evidenced by the following unique combination of characteristics that are outstanding in the new variety and that distinguish it from its parents, as well as from all other varieties of which I am aware:

1. Consistent production of roses in clusters of 5–7 flowers;
2. Good vase life;
3. High petal count;
4. High production per square meter of greenhouse.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—INTERprince (U.S. Plant Pat. No. 8,102).

*Pollen parent.*—Unnamed floribunda seedling.

Classfication:

*Botanical.*—Rosa hybrida.

*Commercial.*—Floribunda.

FLOWER

Observations made from specimens grown in a greenhouse environment at Somis, Calif. from March 1996 to January 1997.

Blooming habit: Recurrent.

Bud:

*Size.*—1¼ inches long when the petals start to unfurl.

*Form.*—The bud form is long, pointed ovoid.

*Color.*—When sepals first divide, bud color is White group 155D. When half blown, the upper sides of the petals are White group 155D; and the lower sides of the petals are White group 155D.

*Sepals.*—Color: Green group 137D. Surface texture: Covered in fine hairs. There are three normally appendaged sepals. There are two unappendaged sepals with hairy edges.

*Receptacle.*—Color: Green group 137D. Shape: Funnel. Size: Small (5/16×¼ inch). Surface: Smooth.

*Peduncle.*—Length: Medium (2 inches to 2¼ inches). Surface: Smooth, with a few small glands. Color: Medium green. Strength: Stiff, erect.

Bloom:

*Size.*—Small. Average open size is 2½ inches.

*Borne.*—Several together in clusters (5 to 7 flowers). Clusters: Pyramidal to flat.

*Stems.*—Medium, strong. Average length is about 18 to 22 inches.

*Form.*—When first open: High centered. Permanence: Flattens; all petals curl, quill fashion.

*Petalage.*—Number of petals under normal conditions: 40 to 45.

*Color.*—The upper sides of the petals are white group 155D. The reverse sides of the petals are white group 155D. The base of each petal has a very small (1/16×1/16 inch) greenish yellow half moon at the point of its attachment. The major color on the upper side is white group 155D.

*Variegations.*—Occasional greenish streak on guard petals.

*Discoloration.*—The general tonality at the end of the first day: No change. At the end of the third day: No change.

*Fragrance.*—Slight.

Petals:

*Texture.*—Thick.

*Shape.*—Deltoid.

*Form.*—Tips slightly recurved; edges slightly quilled.

*Arrangement.*—Imbricated, with a few petaloids in the center.

*Persistence.*—Drop off cleanly.

*Lastingness.*—On the plant: Long (7 days). As a cut flower: Long (10 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Greenish white.

*Stigmas.*—Color: Greenish white.

Form: Bush.

Growth: Vigorous, upright, branching. Height in the greenhouse at the end of one year without pruning is 6 to 7 feet; width is 3½ feet to 4 feet. Will produce stems in excess of 170 per square meter of greenhouse.

Foliage: Number of leaflets on normal mid-stem leaves: 5.

*Size.*—Medium (5×4 inches).

*Quantity.*—Normal.

*Color.*—New foliage: Upper and lower surface is greyed-orange group 176B. Old foliage: Upper surface is green group 137A; lower surface is green group 138C.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth.

*Stipules.*—Medium (½ inch), serrated, bearded.

*Disease resistance.*—Resistant to mildew under normal growing conditions at Somis, Calif. Not tested for rust or blackspot.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Few.

*Form.*—Medium (⅞ inch), hooked slightly downward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by the unique combination of its consistent production of roses in clusters of 5 to 7 flowers; long vase life; high petal count; and high production per square meter of greenhouse.

* * * * *

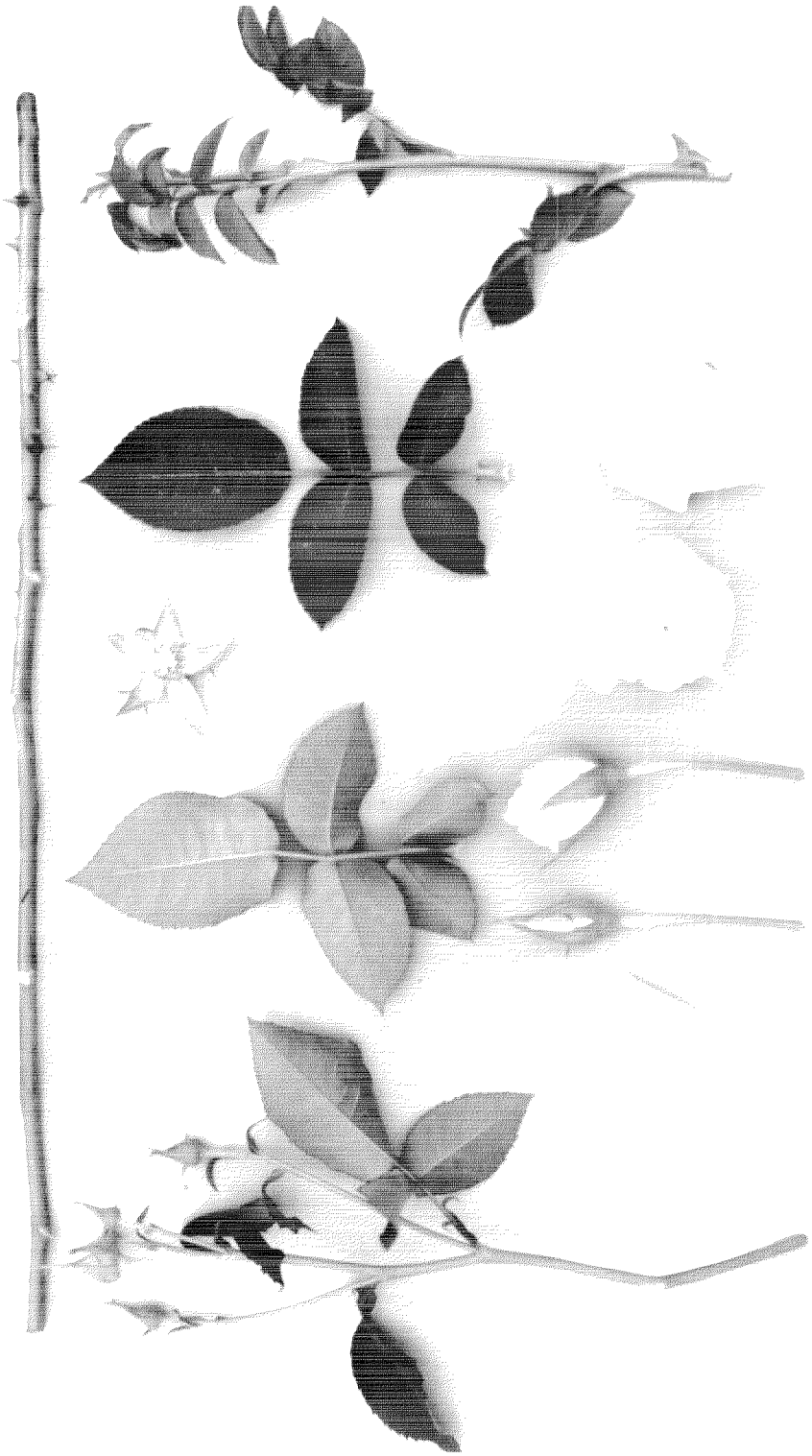
JACess

UNITED STATES PATENT AND TRADEMARK OFFICE

CERTIFICATE OF CORRECTION

PATENT NO. : Plant 10,931

DATED : June 1, 1999

INVENTOR(S) : Keith Zary

It is certified that error appears in the above-indentified patent and that said Letters Patent is hereby corrected as shown below:

On the title page, insert the following:

--Assignee: Bear Creek Gardens, Inc., Medford, Oregon.--

Signed and Sealed this

Twenty-third Day of November, 1999

*Attest:*

Q. TODD DICKINSON

*Attesting Officer*

*Acting Commissioner of Patents and Trademarks*